US012778923B2

(12) United States Patent
Lavedan et al.

(10) Patent No.: US 12,778,923 B2
(45) Date of Patent: *Nov. 3, 2026

(54) METHOD OF TREATMENT

(71) Applicant: Vanda Pharmaceuticals Inc., Washington, DC (US)

(72) Inventors: Christian Lavedan, Potomac, MD (US); Mihael H. Polymeropoulos, Potomac, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 25 days.

This patent is subject to a terminal disclaimer.

(21) Appl. No.: 18/658,100

(22) Filed: May 8, 2024

(65) Prior Publication Data

US 2024/0293355 A1 Sep. 5, 2024

Related U.S. Application Data

(63) Continuation of application No. 17/648,046, filed on Jan. 14, 2022, now abandoned, which is a continuation of application No. 16/848,150, filed on Apr. 14, 2020, now Pat. No. 11,266,622, which is a continuation of application No. 16/211,687, filed on Dec. 6, 2018, now Pat. No. 10,653,665, which is a continuation of application No. 15/326,934, filed as application No. PCT/US2015/047610 on Aug. 29, 2015, now Pat. No. 10,179,119.

(60) Provisional application No. 62/044,856, filed on Sep. 2, 2014, provisional application No. 62/169,635, filed on Jun. 2, 2015.

(51) Int. Cl.
*A61K 31/343* (2006.01)
*A61K 31/00* (2006.01)
*A61K 45/06* (2006.01)

(52) U.S. Cl.
CPC ........... *A61K 31/343* (2013.01); *A61K 31/00* (2013.01); *A61K 45/06* (2013.01)

(58) Field of Classification Search
CPC ........ A61K 31/343; A61K 31/00; A61P 25/20
See application file for complete search history.

(56) References Cited

U.S. PATENT DOCUMENTS

| | | | |
|---|---|---|---|
| 4,044,149 A | 8/1977 | Fields | |
| 4,975,465 A | 12/1990 | Motola | |
| 5,658,919 A | 8/1997 | Ratnaraj | |
| 5,712,310 A | 1/1998 | Koch | |
| 5,840,768 A | 11/1998 | Selinger | |
| 5,856,529 A | 1/1999 | Catt et al. | |
| 5,981,571 A | 11/1999 | Catt | |
| 6,197,348 B1 | 3/2001 | Morella | |
| 6,806,256 B2 | 10/2004 | Ulrich | |
| 9,730,910 B2 | 8/2017 | Dressman et al. | |
| 10,149,829 B2 | 12/2018 | Dressman et al. | |
| 10,179,119 B2 * | 1/2019 | Lavedan | A61K 31/343 |
| 10,376,487 B2 | 8/2019 | Dressman et al. | |
| 10,653,665 B2 * | 5/2020 | Lavedan | A61P 43/00 |
| 11,266,622 B2 * | 3/2022 | Lavedan | A61K 31/00 |
| 11,759,446 B2 * | 9/2023 | Phadke | A61K 31/343 514/469 |
| 2005/0137247 A1 | 6/2005 | Czeisler et al. | |
| 2008/0260837 A1 | 10/2008 | Namburi et al. | |
| 2009/0105333 A1 | 4/2009 | Birznieks et al. | |
| 2012/0136050 A1 | 5/2012 | Polymeropoulos et al. | |
| 2013/0072512 A1 | 3/2013 | Jahagirdar | |
| 2013/0197076 A1 | 8/2013 | Dressman et al. | |
| 2017/0355688 A1 | 12/2017 | Zhao et al. | |

FOREIGN PATENT DOCUMENTS

| | | |
|---|---|---|
| CN | 102675268 A | 9/2012 |
| CN | 106542973 A | 3/2017 |
| KR | 20090105333 A | 10/2009 |
| WO | 2011112167 A1 | 9/2011 |
| WO | 2015108728 A1 | 7/2015 |
| WO | 2016036619 A1 | 3/2016 |
| WO | 2017059877 A1 | 4/2017 |

OTHER PUBLICATIONS

Chinese Office Action for Application No. 202310255914.1 dated Oct. 16, 2004, 6 pages.
Chinese Search Report for Application No. 202310255914.1 dated Oct. 16, 2004, 3 pages.
Peixin Huang et al., "A Traditional Chinese Medicine Treatment for Neurological Diseases," People's Health Publishing House, Oct. 31, 2013, pp. 480-482.
Stephen M Stahl,Cambridge University Press, Stahl's Essential Psychopharmacology—Neurosci entific Basis and Practical Application, Fourth Edition, Dec. 31, 2013.
Anonymous, "Vanda Pharmaceuticals (VNDA) Q2 2013 Earnings Call," Transcript by Seeking Alpha, Jul. 31, 2013 [retrieved on Oct. 14, 2015]. Retrieved from the Internet: <URL:https://www.nasdaq.com/aspx/call-transcript.aspx?StoryId=1591662&Title=vanda-pharmaceuticals-management-discusses-q2-2013-results-earnings-call-transcript>, 2 pages.
Arendt et al., "Melatonin and its agonists: an update," The British Journal of Psychiatry, 2008, vol. 193, pp. 267-269.
Bonacci et al., "Tasimelteon (Hetlioz™): A New Melatonin Receptor Agonist for the Treatment of Non-24-Hour Sleep-Wake Disorder," Journal of Pharmacy Practice, 2015, vol. 28, No. 5, pp. 473-478.
De Leersnyder, H., "Inverted rhythm of melatonin secretion in Smith-Magenis syndrome: from symptoms to treatment," Trends in Endocrinology and Metabolism, 2006, vol. 17, No. 7, pp. 291-298.
Dictionary of Pharmaceutical Excipients, Jul. 25, 2007, pp. 166, 226, and 286.
Ex Parte Quayle Action in U.S. Appl. No. 16/848,150, mailed Sep. 15, 2021, 13 pages.

(Continued)

*Primary Examiner* — Kevin E Weddington
(74) *Attorney, Agent, or Firm* — Hoffman Warnick LLC

(57) ABSTRACT

Embodiments of the invention relate to the treatment of sleep disturbances in individuals with Smith-Magenis Syndrome (SMS).

8 Claims, 6 Drawing Sheets

(56) References Cited

OTHER PUBLICATIONS

Hardeland, R., "New approaches in the management of insomnia: weighing the advantages of prolonged-release melatonin and synthetic melatoninergic agonists," Neuropsychiatric Disease and Treatment, 2009, vol. 5, No. 1, pp. 341-354.
Huang et al., "Clinical Diagnosis and Treatment of Neurology in Traditional Chinese Medicine," People's Medical Publishing House, Oct. 2013, pp. 479-482.
International Search Report and Written Opinion in PCT/US2015/047610, mailed Jan. 11, 2016, 16 pages.
Kulshreshtha et al., Pharmaceutical Suspensions: From Formulation Development to Manufacturing, Springer Science+Business Media, Dec. 2010, 337 pages.
Notice of Allowance in U.S. Appl. No. 16/848,150, mailed Dec. 3, 2021, 7 pages.
Office Action in CN201580046852.7, mailed Feb. 28, 2019, 5 pages.
Office Action in CN201580046852.7, mailed Mar. 13, 2020, 7 pages.
Office Action in CN201580046852.7, mailed Jan. 20, 2021, 9 pages.
Office Action in JP2022535961, mailed Jan. 30, 2024, 4 pages.
Office Action in U.S. Appl. No. 16/848,150, mailed Apr. 14, 2021, 38 pages.
Office Action in U.S. Appl. No. 17/119,953, mailed Apr. 23, 2021, 29 pages.
Park, Brian, "Hetlioz Approved for Nighttime Sleep Disturbances in Smith-Magenis Syndrome," Haymarket Media, Inc., Dec. 3, 2020 [retrieved on Apr. 2, 2021]. Retrieved from the Internet: <URL:https://www.empr.com/home/news/hetlioz-tasimelteon-melatonin-smith-magenis-syndrome-sleep-disturbances>, 7 pages.
Potocki et al., "Circadian Rhythm Abnormalities of Melatonin in Smith-Magenis Syndrome," Journal of Medical Genetics, 2000, vol. 37, pp. 428-433.
Rajarantham et al., "Melatonin agonist tasimelteon (VEC-162) for transient insomnia after sleep-time shift: two randomised controlled multicentre trials," Lancet, Feb. 2009, vol. 373, pp. 482-491.
Sánchez-Barceló et al., "Clinical Uses of Melatonin: Evaluation of Human Trials," Current Medicinal Chemistry, 2010, vol. 17, No. 19, pp. 2070-2095.
Supplementary Search Report in CN201580046852.7, mailed Mar. 13, 2020, 4 pages.
Tasimelteon, Case Analysis, FDA, China Academic Journal Electronic Publishing House, Nov. 12, 2013, vol. 11, No. 8, p. 44.
Vachharajani et al., "Preclinical Pharmacokinetics and Metabolism of BMS-214778, a Novel Melatonin Receptor Agonist," Journal of Pharmacetical Sciences, Apr. 2003, vol. 92, No. 4, pp. 760-772.
Van Thillo et al., "Sleep disturbances in Smith-Magenis syndrome: treatment with melatonin and beta-adrenergic antagonists," Tijdschrift Voor Psychiatrie, Jan. 2010, vol. 52, No. 10, pp. 719-724.
Zhao et al., "Characterisation of the interactive properties of microcrystalline cellulose-carboxymethylhydrogels," International Journal of Pharmaceutics, Mar. 2011, vol. 415, pp. 95-101.
Chinese Office Action for Application No. 201580046852.7, dated Mar. 13, 2020 and English translation thereof, 7 Pages.
International Search Report and Written Opinion in PCT/US2020/064555, mailed Apr. 8, 2021, 13 pages.

* cited by examiner

SUBJID 100-1001 Day 3
Cortisol

SUBJID 100-1001 Day 1
Melatonin

SUBJID 100-1001 Day 3
Melatonin

METHOD OF TREATMENT

CROSS-REFERENCE TO RELATED APPLICATIONS

This application is a continuation application of U.S. patent application Ser. No. 17/648,046, filed 14 Jan. 2022, which is a continuation application of then U.S. patent application Ser. No. 16/848,150, filed 14 Apr. 2020, now U.S. Pat. No. 11,266,622, issued 8 Mar. 2022, which is a continuation application of then U.S. patent application Ser. No. 16/211,687, filed 6 Dec. 2018, now U.S. Pat. No. 10,653,665, issued 19 May 2020, which is a continuation application of then U.S. patent application Ser. No. 15/326,934, filed 17 Jan. 2017, now U.S. Pat. No. 10,179,119, issued 15 Jan. 2019, which is the US National Phase of PCT Patent Application Serial No. PCT/US15/47610, filed 29 Aug. 2015, which claims the benefit of U.S. Provisional Patent Application Ser. Nos. 62/044,856, filed 2 Sep. 2014, and 62/169,635, filed 2 Jun. 2015, each of which is hereby incorporated herein as though fully set forth.

BACKGROUND

Smith-Magenis Syndrome (SMS) is a rare (1 in 25,000 births) clinically-recognizable syndrome resulting from an interstitial deletion of 17p11.2 or a mutation of the RAI1 gene.

SMS is characterized by a distinct pattern of minor craniofacial and skeletal anomalies, expressive speech/language delays, psychomotor and growth retardation, and a striking neurobehavioral phenotype. This phenotype includes stereotypies, self-injurious and aggressive behaviors.

A common symptom of SMS is a chronically disrupted sleep pattern, which is found at all ages. Severe sleep disturbances are virtually universal in SMS patients (75%-100% individuals/caregivers report symptoms), thus representing a major challenge to the patient and family. Sleep disturbances continue across the lifespan; infants typically present with hypersomnolence. Early in life, however, extreme sleep disturbances, including difficulty falling asleep, inability to enter or maintain REM (rapid eye movement) sleep, reduced night sleep, shortened and broken sleep cycles with frequent night-time and early morning awakenings and excessive daytime sleepiness, begin in early toddlerhood and last into adulthood. Furthermore, disturbed sleep appears to be the strongest predictor of maladaptive behavior in children with SMS, including temper tantrums, hyperactivity, attention deficits, and "sleep attacks."

One of the likely contributing factors to these sleep disturbances is an apparent "inverse" circadian pattern of the hormone melatonin which is normally released only at night whereas its production is inhibited by light. Several studies have reported that plasma melatonin in SMS patients is high during the day and low at night, which is opposite of the normal pattern. Whether this apparent "inverted" melatonin secretion pattern is constant within the same individual and universal across SMS patients is still uncertain, as the underlying cause for this disrupted daytime melatonin secretory pattern is unknown. However, findings reported of two patients, whose melatonin secretory pattern and light induced inhibition were normal, are significant because they suggest that the sleep disturbances in SMS may not be solely attributed to the abnormal diurnal melatonin secretion.

Significant progress has been made in the understanding of the genetic basis of the SMS syndrome. However, the molecular basis of the circadian rhythm disruption and of other specific features of the phenotype have not been fully characterized and a greater understanding of the cellular and molecular control of both the circadian clock and pineal functioning will provide options for pharmacological interventions that could address the most severe symptoms of the disease. Until a precise understanding of the biological anomaly present in SMS is obtained, treatment with conventional drugs, like beta-blockers and exogenous melatonin (in the US), will not satisfactorily improve aberrant sleep patterns and behavior in SMS patients and therefore will not consistently ease the burden on patients and their families. At the present time, there is no effective treatment for sleep disturbances in SMS.

SUMMARY OF THE INVENTION

In one embodiment, the invention provides a method for the treatment of sleep disturbances in a patient with SMS that comprises internally administering to the patient an effective amount of tasimelteon daily.

In another embodiment, the invention provides a method of treating a sleep disorder in an individual suffering from SMS, the method comprising: inhibiting melatonin production in the individual during waking hours; and administering to the individual an effective amount of a melatonin agonist prior to sleep.

In another embodiment, the invention provides a method of regulating melatonin production in an individual exhibiting light-induced melatonin production, the method comprising: inhibiting melatonin production in the individual during waking hours; and stimulating melatonin production in the individual during sleep.

In still another embodiment, the invention provides a method of treating a sleep disorder in an individual suffering from SMS, the method comprising: inhibiting melatonin production in the individual during waking hours; and stimulating melatonin production in the individual during sleep.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

Figure 1:
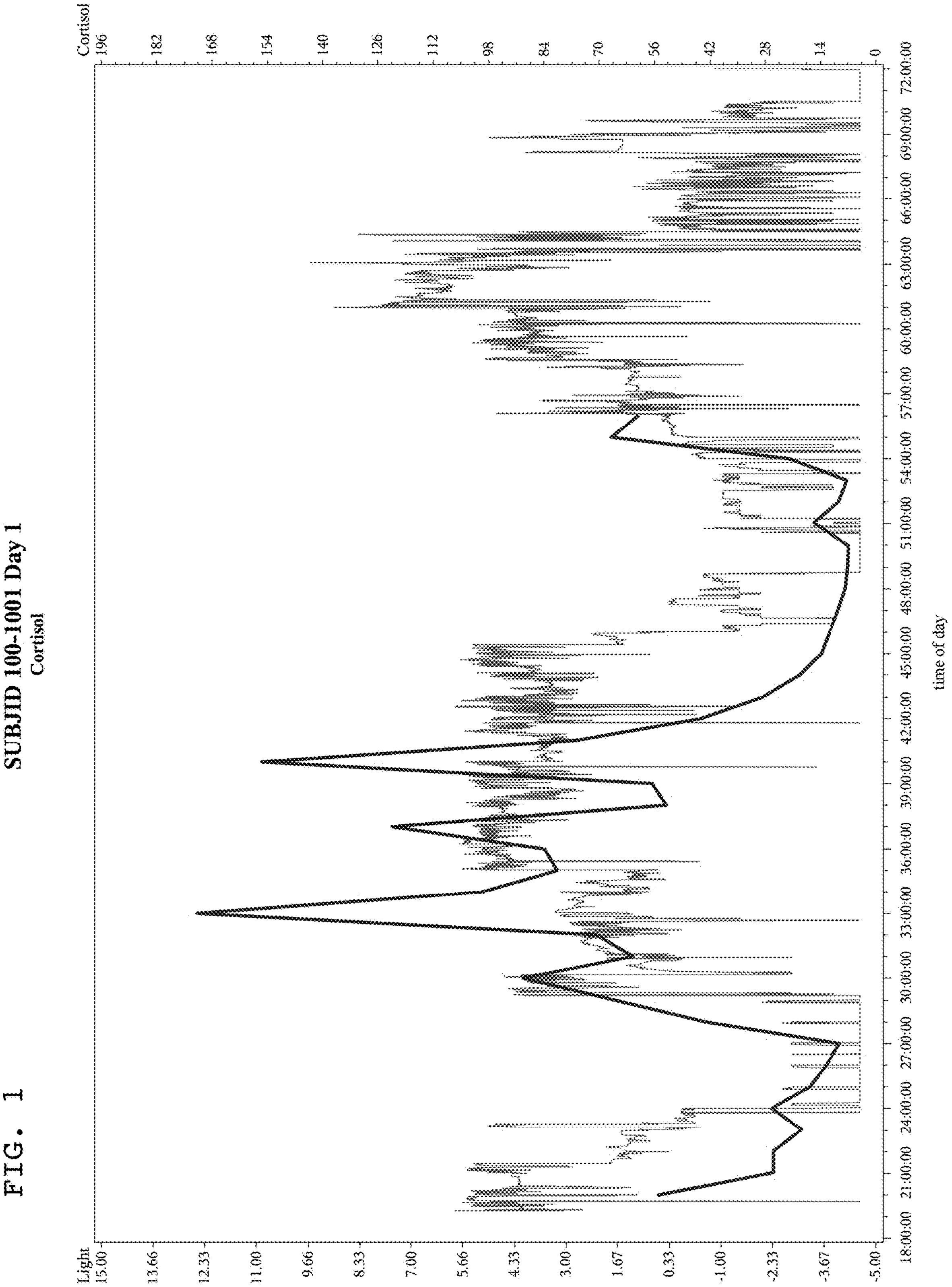
FIGS. 1-3 show measured cortisol levels and light exposure levels for an individual with SMS during three consecutive days of a study.

It is noted that the drawings of the invention are not to scale. The drawings are intended to depict only typical aspects of the invention, and therefore should not be considered as limiting the scope of the invention.

DETAILED DESCRIPTION

Applicants have carried out a study with the objectives to characterize the circadian rhythms of individuals with SMS as measured by plasma melatonin and cortisol, evaluate if there is an association between the melatonin or cortisol circadian patterns (delayed, advanced, Non-24, variable) and various aspects of the SMS phenotype (ex: sleeping patterns, behavioral problems), determine if there is an association between the characteristics of the genetic mutation (e.g., extent of the 17p11.2 deletion, RAI1 mutation) and the levels and circadian patterns of melatonin and cortisol and/or the response to a melatonin suppression test (MST), and assess light sensitivity in individuals with SMS as determined by a Melatonin Suppression Test (MST).

This study consisted of three phases: a screening phase followed by an evaluation phase with an optional variable phase for subjects whose circadian melatonin profile warrants further investigation.

During the screening phase, participants were provided consent/assent and initial eligibility was evaluated. Subjects were asked to provide information regarding their prior SMS diagnosis, to complete all baseline behavioral assessments and quality of life questionnaires, and allow a blood sample to be obtained for genetic testing. Samples were sent to a core genetic laboratory for a detailed analysis of the RAI1 gene. Results of the analysis did not need to be returned before subject began the trial if the diagnosis meet eligibility criteria.

During the evaluation phase, three testing segments (TS1, TS2, and TS3) were conducted one week apart at weeks 1, 2, and 4, respectively. These segments included 36-hour melatonin and cortisol assessments where blood samples were taken every hour from an indwelling catheter. When the subject arrived for TS1, they were fitted with an actigraphy watch to assess light exposure and monitor activity. Blood samples were begun on the first night at 20:00 hours and continued hourly for 36 hours during each testing period.

The variable phase consisted of an optional melatonin suppression test (MST) for individuals determined to have a delayed, advanced, or Non-24 circadian profile. During the MST, plasma samples were collected every hour for the measurement of melatonin. One to two hours after melatonin onset, subjects were exposed to bright light for 180 minutes, with the exposure timed to coincide with the expected peak in plasma melatonin concentrations. During the period of light exposure, blood samples were collected every 30 minutes.

Results

Eight participants, aged 7 to 35, with history of severe sleep disturbances and a cytogenetic confirmed SMS diagnosis completed the evaluation phase. The timing of the melatonin and cortisol acrophases was consistent during the 4 week assessment, with a circadian period of ~24.0 hours. Melatonin secretion occurred mainly during the daytime hours with a mean acrophase between approximately 2:00 am and 5:30 pm and very low levels or no melatonin produced during the nighttime, except for one participant for whom the melatonin secretion acrophase occurred around 5:00 am. The mean cortisol acrophase ranged from about 9:00 am to 11:30 am in all participants. The sleep/wake pattern recorded by actigraphy showed a severely fragmented nighttime sleep period with multiple bouts of activity, and daytime naps or periods of no or little activity. These patterns were variable between participants and between days.

Individuals with SMS showed an abnormal daytime, but stable, secretion pattern of plasma melatonin believed to be responsible for the severe sleep disorder. In contrast, their cortisol rhythm appears to be normal. Individuals with SMS suffer from severe nighttime sleep disturbances characterized in particular by multiple periods of nighttime activity that frequently interrupt the sleep period, resulting in poor sleep efficiency, variable sleep onset and morning awakenings, and unpredictable sleep quality.

The sleep disorder, which is believed to be the strongest predictor of maladaptive behavior in SMS individuals, including aggressive behavior, temper tantrums, hyperactivity, attention deficits, constitutes a major challenge to the patients and their families. Its detailed characterization is essential in developing an effective treatment, which is crucially needed.

Tasimelteon

Tasimelteon is a circadian regulator which binds specifically to two high affinity melatonin receptors, Mel1a (MT1R) and Mel1b (MT2R). These receptors are found in high density in the suprachiasmatic nucleus of the brain (SCN), which is responsible for synchronizing our sleep/wake cycle. Tasimelteon has been shown to improve sleep parameters in prior clinical studies, which simulated a desynchronization of the circadian clock. Tasimelteon has so far been studied in hundreds of individuals and has shown a good tolerability profile.

Tasimelteon has the chemical name: trans-N-[[2-(2,3-dihydrobenzofuran-4-yl)cycloprop-1yl]methyl]propanamide, has the structure of Formula I.

Formula I

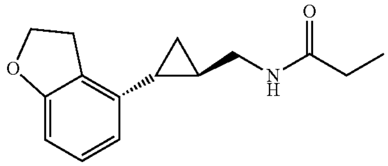

Tasimelteon is disclosed in U.S. Pat. No. 5,856,529 and in US Patent Application Publication No. 2009/0105333, both of which are incorporated herein by reference as though fully set forth.

Tasimelteon is a white to off-white powder with a melting point of about 78° C. (DSC) and is very soluble or freely soluble in 95% ethanol, methanol, acetonitrile, ethyl acetate, isopropanol, polyethylene glycols (PEG-300 and PEG-400), and only slightly soluble in water. The native pH of a saturated solution of tasimelteon in water is 8.5 and its aqueous solubility is practically unaffected by pH. Tasimelteon has 2-4 times greater affinity for MT2R relative to MT1R. Its affinity ($K_i$) for MT1R is 0.3 to 0.4 and for MT2R, 0.1 to 0.2. Tasimelteon is useful in the practice of this invention because it is a melatonin agonist.

In related aspects, this invention relates to the use of a tasimelteon metabolite as the melatonin agonist. Tasimelteon metabolites include, for example, a phenol-carboxylic acid analog (M9) and a hydroxypropyl-phenol analog (M11). Each is formed in humans following oral administration of tasimelteon.

Specifically, aspects of the invention encompass use of tasimelteon or of compounds of Formulas II or III, including salts, solvates, and hydrates of tasimelteon or of compounds of Formula II or Formula III, in amorphous or crystalline form.

Formula II

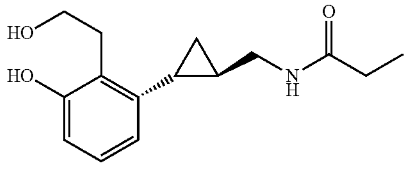

(M11)

Formula III

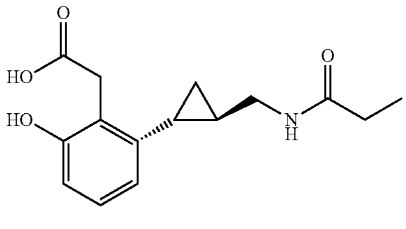

(M9)

While depicted herein in the R-trans configuration, the invention nevertheless comprises use of stereoisomers thereof, i.e., R-cis, S-trans, and S-cis. In addition, the invention comprises use of prodrugs of tasimelteon or of compounds of Formula II or of Formula III, including, for example, esters of such compounds. The discussion that follows will refer to tasimelteon but it is to be understood that the compounds of Formula II and III are also useful in the practice of aspects of the invention.

Metabolites of tasimelteon include, for example, those described in "Preclinical Pharmacokinetics and Metabolism of BMS-214778, a Novel Melatonin Receptor Agonist" by Vachharajani et al., J. Pharmaceutical Sci., 92(4):760-772, which is hereby incorporated herein by reference. The active metabolites of tasimelteon can also be used in the method of this invention, as can pharmaceutically acceptable salts of tasimelteon or of its active metabolites. For example, in addition to metabolites of Formula II and III, above, metabolites of tasimelteon also include the monohydroxylated analogs M13 of Formula IV, M12 of Formula V, and M14 of Formula VI.

Formula IV

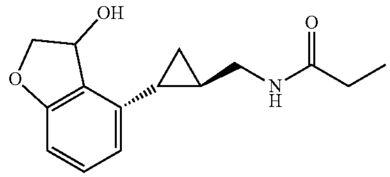

Formula V

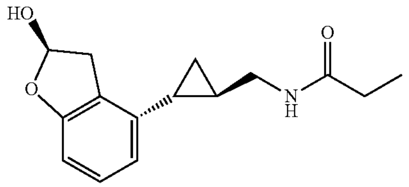

-continued

Formula VI

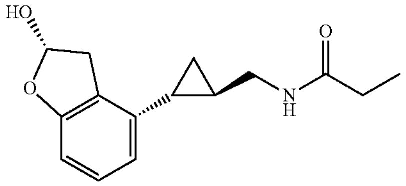

Tasimelteon can be synthesized by procedures known in the art. The preparation of a 4-vinyl-2,3-dihydrobenzofuran cyclopropyl intermediate can be carried out as described in U.S. Pat. No. 7,754,902, which is incorporated herein by reference as though fully set forth.

Pro-drugs, e.g., esters, and pharmaceutically acceptable salts can be prepared by exercise of routine skill in the art.

Treatment of SMS-Related Sleep Disturbances

Figure 2:
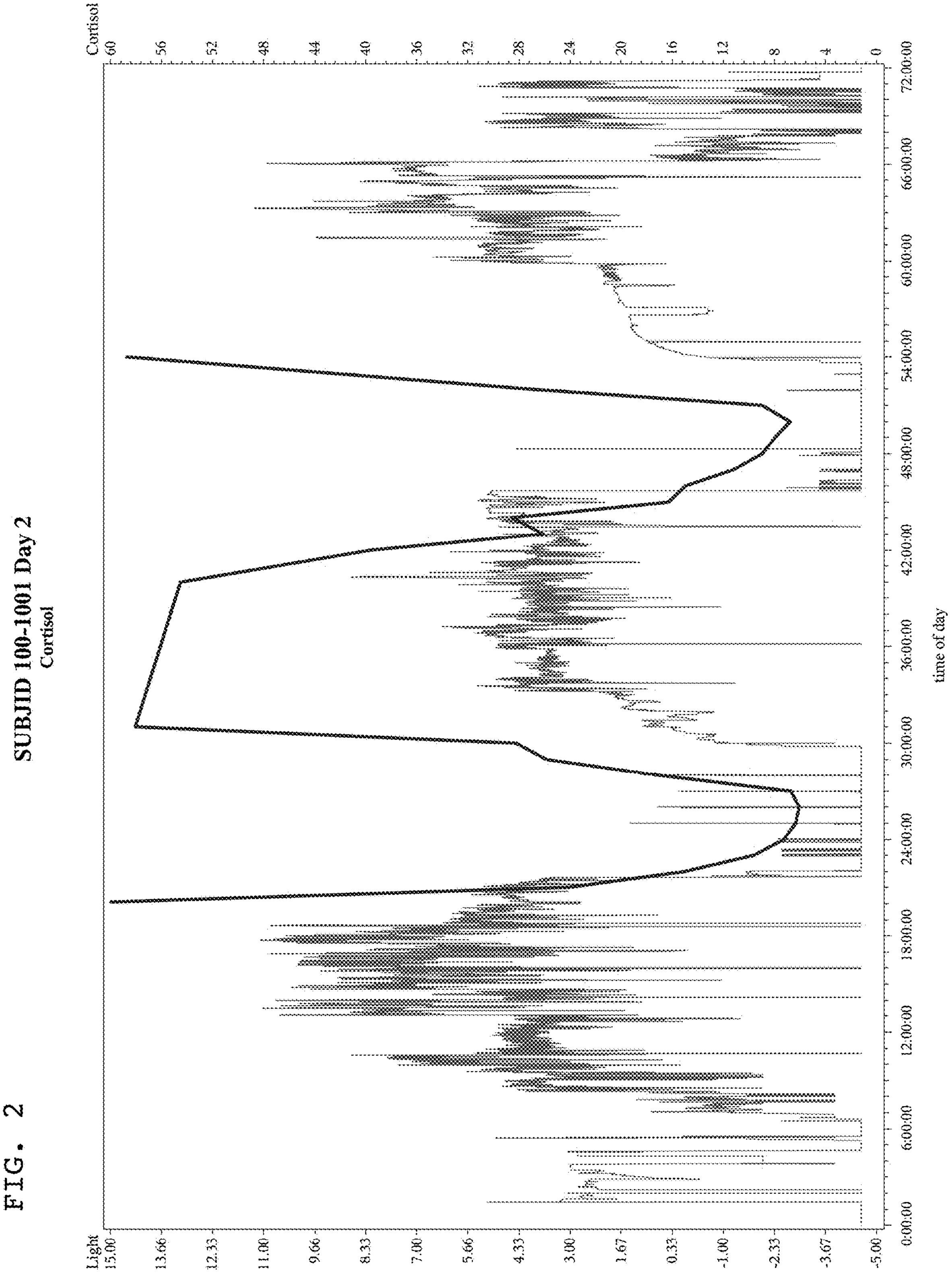
Figure 3:
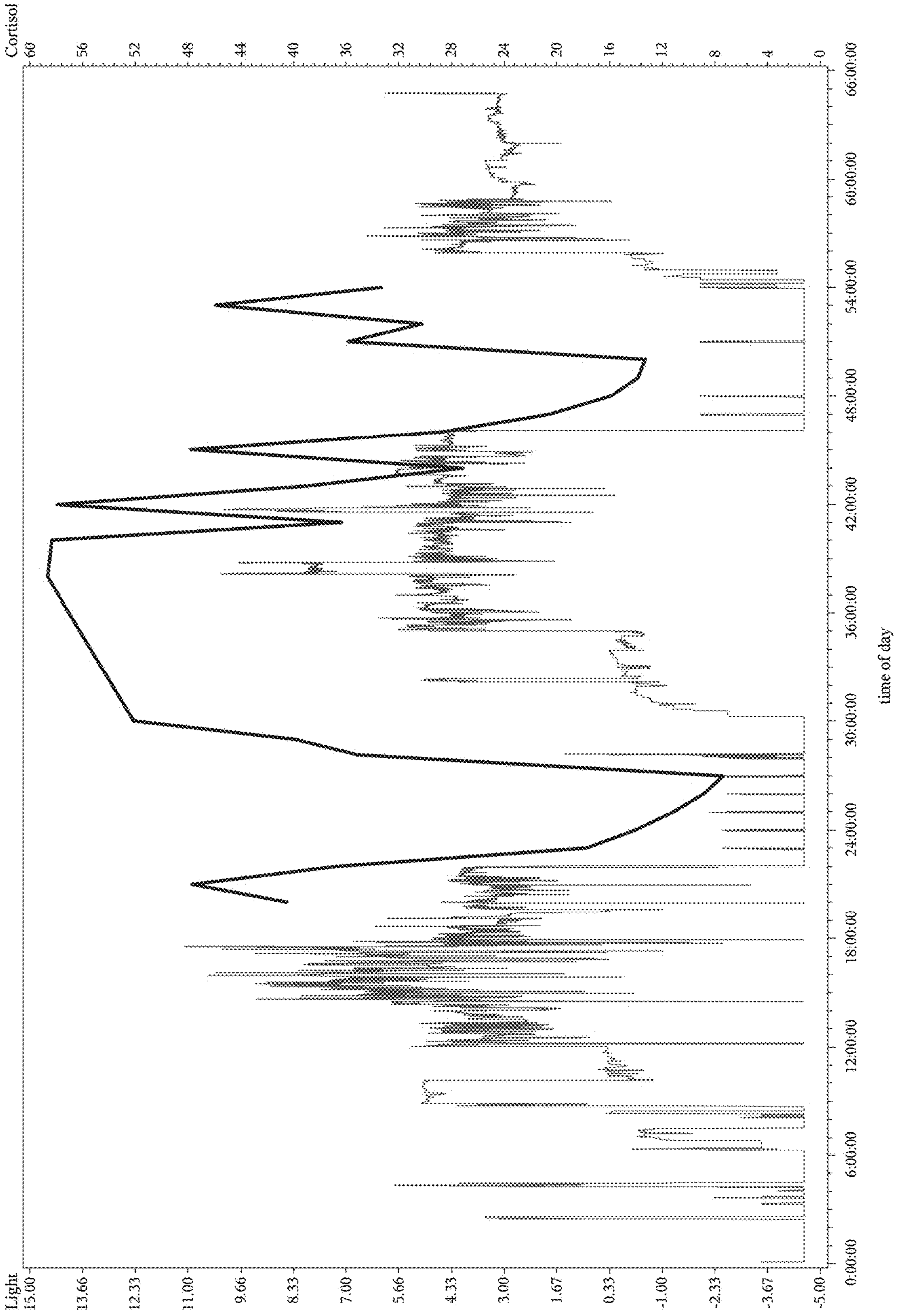
Figure 4:
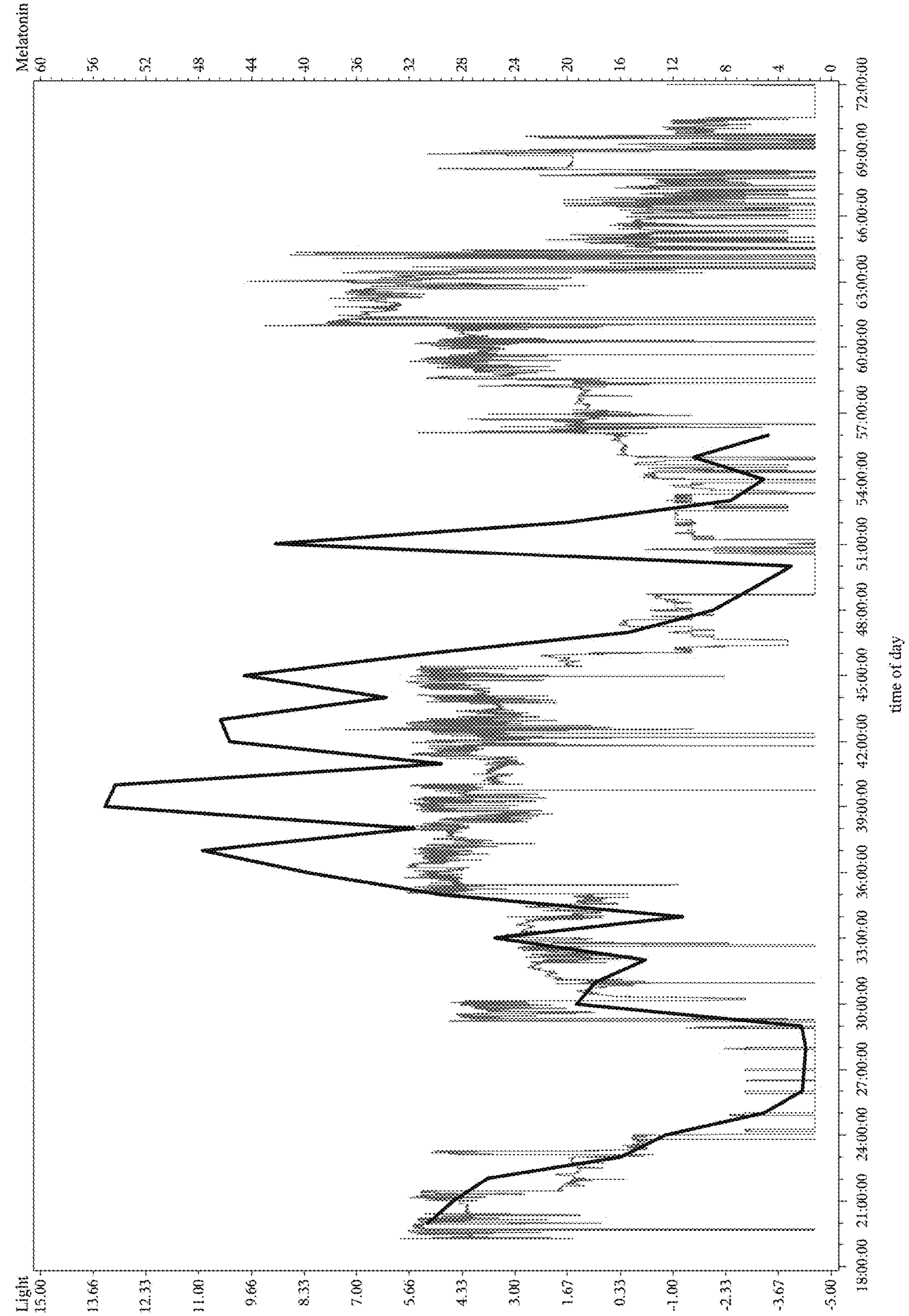
FIGS. 4-6 show measured melatonin levels and light exposure levels for an individual with SMS during three consecutive days of a study.
Figure 5:
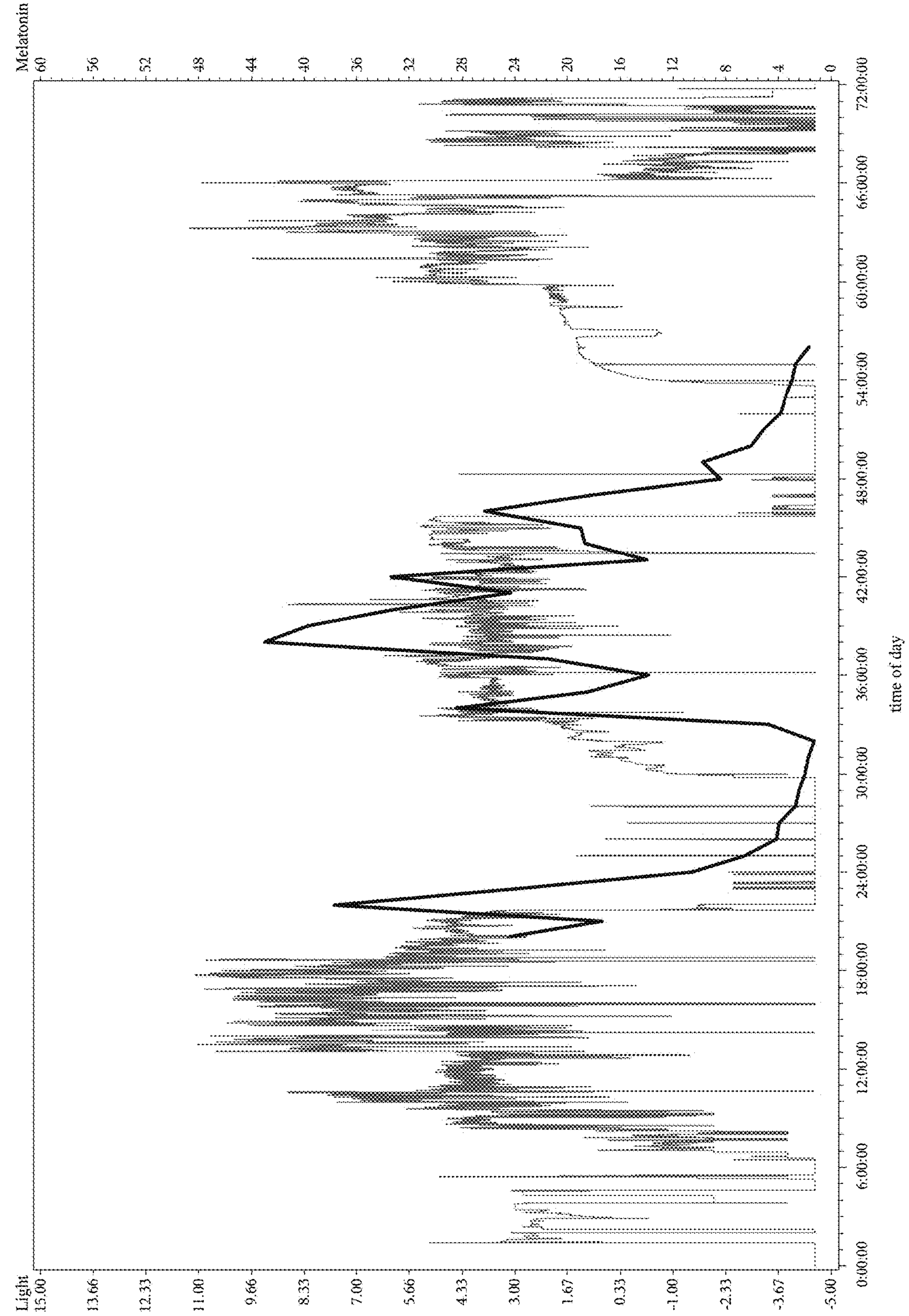
Figure 6:
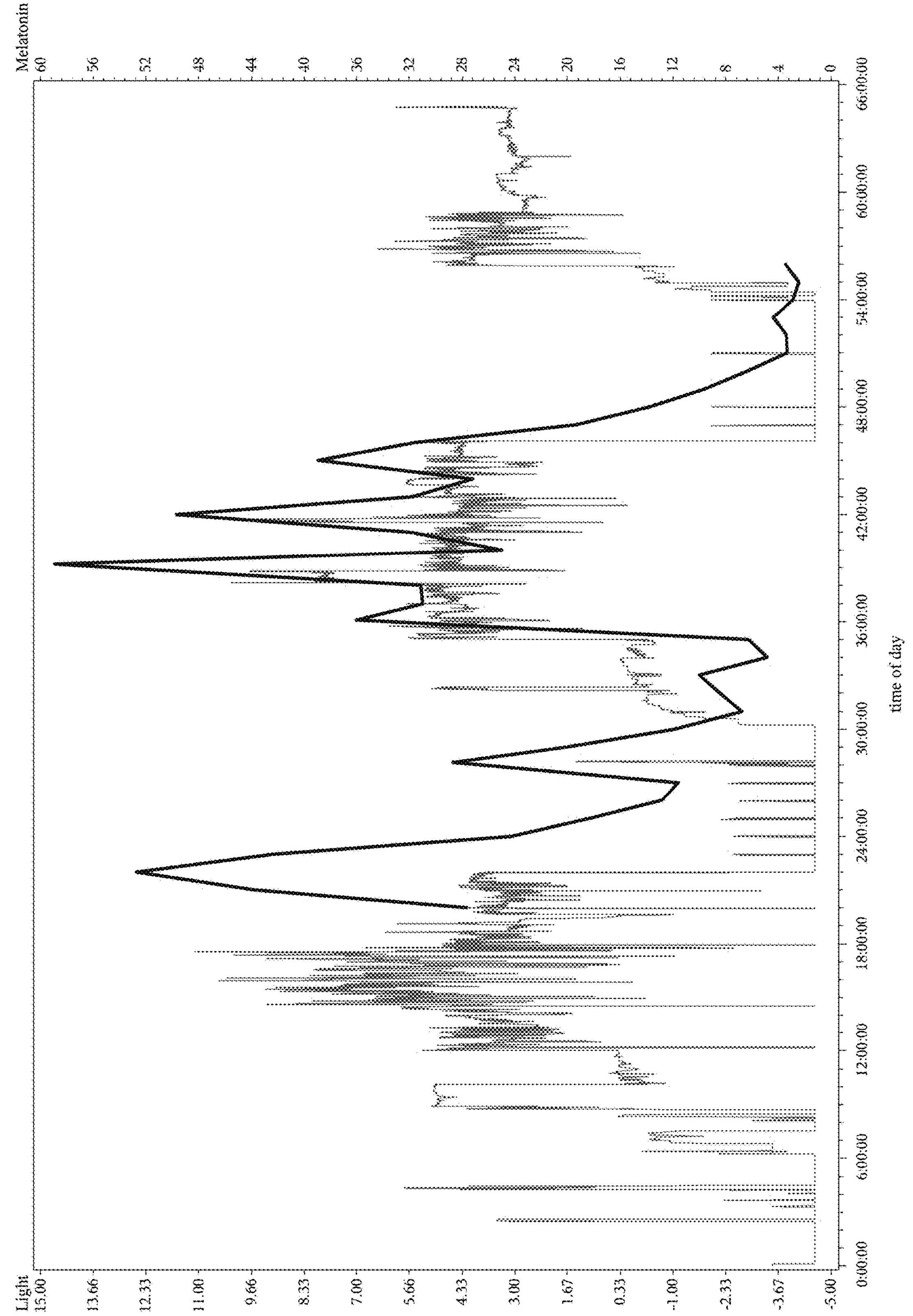

In at least some individuals with SMS, melatonin production increases with light exposure—light-induced melatonin production—a pattern opposite that expected. For example, FIGS. 4-6 show melatonin secretion (thick line) and a patient's light exposure (thin line) during days 1, 2, and 3 of the study. A strong correlation is seen between light exposure and melatonin production. FIGS. 1-3 show similar results for a patient's cortisol secretion (thick line).

The disrupted sleep patterns of SMS patients—or other individuals exhibiting light-induced melatonin production—may be treated by inhibiting melatonin production during waking hours and/or increasing melatonin production during sleep. For example, melatonin production may be inhibited by reducing exposure of the individual's eyes to light using, for example, light blocking or light filtering eyewear. Such eyewear may include eyeglasses, contact lenses, etc., as will be apparent to one skilled in the art. Light filtering eyewear may be operable to filter a broad spectrum of light or, for example, a wavelength or range of wavelengths determined to stimulate melatonin production.

In other embodiments of the invention, melatonin production may be inhibited by administering to the individual an effective amount of a beta blocker. In some embodiments of the invention, such administration may be made using a device operable to deliver to the individual a dosage of a beta blocker in proportion to the individual's exposure to light as measured, for example, using a light sensor, light meter, or similar apparatus in communication with or incorporated into the device.

Increasing melatonin production may include administering a melatonin agonist to the individual. In some embodiments of the invention, the melatonin agonist may be tasimelteon and may be administered at a dosage of between about 5 mg and 100 mg, e.g., between about 20 mg and about 50 mg, e.g., about 20 mg once daily prior to sleep, e.g., between about 0.5 hours and about 1.5 hours prior to sleep, e.g., about 1 hour prior to sleep.

Improvements in sleep disturbances may be measured in any number of ways, including, for example, improvement in nighttime sleep, which may include a reduction in the percentage of wake period within the patient's sleep interval; improvement in one or more of the following: total amount of nighttime sleep; number, timing, and length of nighttime awakenings; sleep onset; wake time; number, timing, and length of daytime naps; improvement in clinical global impression of change (CGI-C); improvement in clinical global impression of severity (CGI-S); and improvement in behavior.

In the case of treatment with tasimelteon administration, treatment effects may be maintained by ongoing daily administration of tasimelteon. Tasimelteon administration may, according to some embodiments of the invention, be combined with the inhibition of melatonin activity in the patient during waking hours by, for example, one or more of: reducing the exposure of the patient's eyes to light, internally administering to the patient an active pharmaceutical ingredient that inhibits melatonin production, or internally administering to the patient an active pharmaceutical ingredient that antagonizes melatonin activity Other aspects and embodiments of the invention will be apparent to one skilled in the art from the description above and the appended summary of the study and are within the scope of the invention.

What is claimed is:

1. A method of treating a patient suffering from Smith-Magenis Syndrome (SMS), the method comprising:

administering to the patient tasimelteon in an amount effective to improve sleep in the patient.

2. The method of claim 1, wherein improved sleep includes one or more of the following:

increasing total nighttime sleep; or reducing nighttime awakenings; or advancing sleep onset; or reducing wake time; or reducing daytime naps.

3. The method of claim 2, wherein reducing nighttime awakenings includes reducing a number of nighttime awakenings, reducing a length of nighttime awakenings, or both.

4. The method of claim 2, wherein administering includes administering the tasimelteon once daily between one-half hour and two hours before bedtime.

5. The method of claim 4, wherein administering includes administering the tasimelteon between one-half hour and one-and-one-half hours before bedtime.

6. The method of claim 5, wherein administering includes administering the tasimelteon one hour before bedtime.

7. The method of claim 1, wherein the amount of tasimelteon effective to improve sleep in the patient is between about 5 mg/day and about 100 mg/day.

8. The method of claim 7, wherein the amount of tasimelteon effective to improve sleep in the patient is about 20 mg/day.

* * * * *